United States Patent
Rasmussen et al.

(10) Patent No.: US 9,950,117 B2
(45) Date of Patent: Apr. 24, 2018

(54) MEDICAL DEVICE AND CARTRIDGE

(71) Applicant: Novo Nordisk A/S, Bagsvaerd (DK)

(72) Inventors: Henrik Rasmussen, Fredensborg (DK); Bo Erik Lennart Berggren, Lund (SE); Bodo von Muenchow, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/180,820

(22) Filed: Jun. 13, 2016

(65) Prior Publication Data

US 2016/0296702 A1 Oct. 13, 2016

Related U.S. Application Data

(62) Division of application No. 13/148,868, filed as application No. PCT/EP2010/051804 on Feb. 12, 2010.

(Continued)

(30) Foreign Application Priority Data

Feb. 13, 2009 (EP) ..................................... 09152862

(51) Int. Cl.
*A61B 19/00* (2006.01)
*A61M 5/24* (2006.01)
(Continued)

(52) U.S. Cl.
CPC ............. *A61M 5/24* (2013.01); *G06K 19/067* (2013.01); *G09F 3/0291* (2013.01);
(Continued)

(58) Field of Classification Search
CPC ................ A61M 5/24; A61M 5/31533; A61M 2005/2488; A61M 2005/2492;
(Continued)

(56) References Cited

U.S. PATENT DOCUMENTS 3,644,715 A 2/1972 Holderith
3,700,862 A 10/1972 Snook et al.
(Continued)

FOREIGN PATENT DOCUMENTS

CN 1051152 A 5/1991
CN 1013704 8/1991
(Continued)

*Primary Examiner* — Philip R Wiest
(74) *Attorney, Agent, or Firm* — Wesley Nicolas (57) ABSTRACT

A cartridge engageable with a medical device, the method of making a cartridge comprising an ordered arrangement of N electrical components each with different respective values of an electrical property, and an ordered arrangement of N conductors operably coupled to the ordered arrangement of the N electrical components.

A medical device is arranged to receive a cartridge comprises for each of N conductors on the cartridge, at least a first respective contact arranged to electrically couple with the corresponding conductor when the cartridge is engaged with the medical device; the medical device also comprises an evaluation means operable to evaluate the different respective values of an electrical property of N electrical components on the cartridge, wherein the N electrical components form an ordered arrangement which is operably coupled to the N conductors on the cartridge, and a switching arrangement operable to selectively electrically couple a respective pair of contacts to said evaluation means.

9 Claims, 7 Drawing Sheets

Related U.S. Application Data (60) Provisional application No. 61/155,174, filed on Feb. 25, 2009.

(51) Int. Cl.
  *G06K 19/067* (2006.01)
  *G09F 3/00* (2006.01)
  *A61M 5/315* (2006.01)

(52) U.S. Cl.
  CPC ..... *A61M 5/31525* (2013.01); *A61M 5/31533* (2013.01); *A61M 2005/2488* (2013.01); *A61M 2005/2492* (2013.01); *A61M 2205/6027* (2013.01); *A61M 2207/00* (2013.01); *Y10T 29/49002* (2015.01)

(58) Field of Classification Search
  CPC ...... A61M 2205/6027; A61M 2207/00; G06K 19/067; G09F 3/0291; Y10T 29/49002; A61J 1/10; A61J 1/2096; A61J 2001/201
  See application file for complete search history.

(56) References Cited

U.S. PATENT DOCUMENTS

| | | |
|---|---|---|
| 3,809,863 A | 5/1974 | Oberg |
| 3,916,157 A | 10/1975 | Roulette et al. |
| 3,998,513 A | 12/1976 | Kobayashi et al. |
| 4,179,212 A | 12/1979 | Lahr |
| 4,327,283 A | 4/1982 | Heyman et al. |
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,499,371 A | 2/1985 | Rose |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz et al. |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur, III |
| 5,004,897 A | 4/1991 | Biggio et al. |
| 5,053,715 A | 10/1991 | Andermo |
| 5,059,776 A | 10/1991 | Antes |
| 5,077,635 A | 12/1991 | Bollhagen et al. |
| 5,078,683 A | 1/1992 | Sancoff et al. |
| 5,091,798 A | 2/1992 | Hibino |
| 5,132,026 A | 7/1992 | Baluyot et al. |
| 5,153,827 A | 10/1992 | Coutre et al. |
| 5,159,181 A | 10/1992 | Bartels et al. |
| 5,174,766 A | 12/1992 | Yoshizawa et al. |
| 5,176,502 A | 1/1993 | Sanderson et al. |
| 5,196,683 A | 3/1993 | Marom et al. |
| 5,271,527 A | 12/1993 | Haber et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate, Jr. |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | Colgate, Jr. et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent et al. |
| 5,681,285 A | 10/1997 | Ford et al. |
| 5,686,725 A | 11/1997 | Maruyama et al. |
| 5,704,922 A | 1/1998 | Brown |
| 5,720,733 A | 2/1998 | Brown |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,791,880 A | 8/1998 | Wilson |
| 5,792,117 A | 8/1998 | Brown |
| 5,793,502 A | 8/1998 | Bianco et al. |
| 5,821,521 A | 10/1998 | Bridgelall et al. |
| 5,821,524 A | 10/1998 | Horlbeck et al. |
| 5,876,380 A | 3/1999 | Manganini et al. |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,920,198 A | 7/1999 | Suzuki et al. |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown |
| 6,090,064 A | 7/2000 | Reilly et al. |
| 6,110,148 A | 8/2000 | Brown |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,230,927 B1 | 5/2001 | Schoonen et al. |
| 6,265,466 B1 | 7/2001 | Glatkowski et al. |
| 6,274,092 B1 | 8/2001 | Itoh |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,743,202 B2 | 6/2004 | Hirschman et al. |
| 6,813,868 B2 | 11/2004 | Baldwin et al. |
| 6,854,653 B2 | 2/2005 | Eilersen |
| 6,859,673 B2 | 2/2005 | Steffen |
| 6,876,209 B2 | 4/2005 | Lin et al. |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries, Jr. et al. |
| 7,061,831 B2 | 6/2006 | De La Huerga |
| 7,077,332 B2 | 7/2006 | Verschuur et al. |
| 7,104,973 B2 | 9/2006 | Woolston et al. |
| 7,108,184 B2 | 9/2006 | Mase et al. |
| 7,138,806 B2 | 11/2006 | Gafner et al. |
| 2001/0001472 A1 | 5/2001 | Sano et al. |
| 2001/0013544 A1 | 8/2001 | Rathus et al. |
| 2001/0015202 A1 | 8/2001 | Miller |

(56) References Cited

U.S. PATENT DOCUMENTS

| | | | |
|---|---|---|---|
| 2001/0034506 A1* | 10/2001 | Hirschman | A61M 5/14546 604/207 |
| 2002/0000471 A1 | 1/2002 | Aasmul et al. | |
| 2002/0012176 A1 | 1/2002 | Ning | |
| 2002/0020654 A1 | 2/2002 | Eilersen | |
| 2002/0022821 A1 | 2/2002 | Eilersen | |
| 2002/0063156 A1 | 5/2002 | Marchand | |
| 2002/0106309 A1 | 8/2002 | Mathus et al. | |
| 2002/0117549 A1 | 8/2002 | Lee | |
| 2002/0117579 A1 | 8/2002 | Kotoulas et al. | |
| 2002/0123078 A1 | 9/2002 | Seul et al. | |
| 2003/0006209 A1 | 1/2003 | Stefen et al. | |
| 2003/0015590 A1 | 1/2003 | Chen | |
| 2003/0039590 A1 | 2/2003 | Lodge | |
| 2003/0116630 A1 | 6/2003 | Carey et al. | |
| 2003/0125670 A1 | 7/2003 | Langley et al. | |
| 2003/0143614 A1 | 7/2003 | Drmanac | |
| 2003/0205625 A1 | 11/2003 | Eilersen | |
| 2003/0233069 A1 | 12/2003 | Gillespie et al. | |
| 2004/0008853 A1 | 1/2004 | Pelrine et al. | |
| 2004/0024368 A1 | 2/2004 | Broselow | |
| 2004/0046032 A1 | 3/2004 | Urano et al. | |
| 2004/0051368 A1 | 3/2004 | Caputo et al. | |
| 2004/0141426 A1 | 7/2004 | Kawasaki et al. | |
| 2004/0155113 A1 | 8/2004 | Urano et al. | |
| 2004/0178255 A1 | 9/2004 | Eich et al. | |
| 2004/0200558 A1 | 10/2004 | Stevens et al. | |
| 2004/0207385 A1 | 10/2004 | Gafner et al. | |
| 2004/0210199 A1 | 10/2004 | Atterbury et al. | |
| 2005/0006472 A1 | 1/2005 | Verschuur et al. | |
| 2005/0035207 A1 | 2/2005 | Philyaw et al. | |
| 2005/0060059 A1 | 3/2005 | Klein et al. | |
| 2005/0116033 A1 | 6/2005 | Moore | |
| 2005/0156318 A1 | 7/2005 | Douglas | |
| 2005/0182360 A1 | 8/2005 | Yeandel et al. | |
| 2005/0236603 A1 | 10/2005 | Faris | |
| 2005/0283116 A1 | 12/2005 | Eakins et al. | |
| 2006/0097877 A1 | 5/2006 | Baba et al. | |
| 2006/0118612 A1 | 6/2006 | Christoffersen et al. | |
| 2006/0125491 A1 | 6/2006 | Grishin et al. | |
| 2006/0129104 A1 | 6/2006 | Cowan et al. | |
| 2006/0138233 A1 | 6/2006 | Kemppainen et al. | |
| 2006/0164002 A1 | 7/2006 | O'Brien et al. | |
| 2006/0170981 A1 | 8/2006 | Ricks et al. | |
| 2006/0175427 A1 | 8/2006 | Jonientz et al. | |
| 2006/0176267 A1 | 8/2006 | Honeyman et al. | |
| 2006/0224123 A1 | 10/2006 | Friedli et al. | |
| 2006/0226238 A1 | 10/2006 | Salib et al. | |
| 2006/0243804 A1 | 11/2006 | Christoffersen et al. | |
| 2007/0080234 A1 | 4/2007 | Domoy | |
| 2007/0239116 A1 | 10/2007 | Follman et al. | |
| 2008/0015510 A1 | 1/2008 | Sandoz et al. | |
| 2008/0306443 A1* | 12/2008 | Neer | A61M 5/007 604/121 |
| 2009/0088701 A1 | 4/2009 | Larsen | |
| 2010/0194537 A1 | 8/2010 | Nielsen et al. | |

FOREIGN PATENT DOCUMENTS

| | | |
|---|---|---|
| DE | 2636634 A1 | 2/1978 |
| DE | 3236374 A1 | 4/1984 |
| DE | 3712089 A1 | 10/1988 |
| DE | 4020522 A1 | 1/1992 |
| DE | 4234016 A1 | 4/1993 |
| DE | 4402319 A1 | 8/1994 |
| DE | 19504111 A1 | 8/1995 |
| DE | 19637967 A1 | 10/1997 |
| DE | 19814687 C1 | 2/1999 |
| DE | 10035192 C1 | 10/2001 |
| DE | 10051575 A1 | 2/2002 |
| EP | 235691 A2 | 9/1987 |
| EP | 248165 A2 | 12/1987 |
| EP | 336778 A2 | 10/1989 |
| EP | 364010 A2 | 4/1990 |
| EP | 398717 A2 | 11/1990 |
| EP | 402553 A1 | 12/1990 |
| EP | 422482 A2 | 4/1991 |
| EP | 492954 A2 | 7/1992 |
| EP | 573129 A2 | 12/1993 |
| EP | 588427 A2 | 3/1994 |
| EP | 626660 A2 | 11/1994 |
| EP | 685810 A1 | 12/1995 |
| EP | 690457 A2 | 1/1996 |
| EP | 716290 A2 | 6/1996 |
| EP | 833273 A2 | 4/1998 |
| EP | 833278 A2 | 4/1998 |
| EP | 911859 A1 | 4/1999 |
| EP | 1095668 A1 | 5/2001 |
| EP | 1142643 A2 | 10/2001 |
| EP | 1143643 A2 | 10/2001 |
| EP | 1193641 A2 | 4/2002 |
| EP | 1246127 A2 | 10/2002 |
| EP | 1462134 A1 | 9/2004 |
| EP | 1503185 A2 | 2/2005 |
| FR | 2771111 A1 | 5/1999 |
| GB | 2088163 A | 6/1982 |
| GB | 2159007 A | 11/1985 |
| GB | 2216259 A | 10/1989 |
| GB | 2287551 A | 9/1995 |
| GB | 2309801 A | 8/1997 |
| GB | 2336927 A | 11/1999 |
| GB | 2341965 A | 3/2000 |
| JP | 56-094475 A | 7/1981 |
| JP | 59-131917 A | 7/1984 |
| JP | 63-100303 A | 5/1988 |
| JP | 2-085370 A | 3/1990 |
| JP | 2-188702 A | 7/1990 |
| JP | 2-250083 A | 10/1990 |
| JP | 3-027037 A | 2/1991 |
| JP | 4-222084 A | 8/1992 |
| JP | 4-233624 A | 8/1992 |
| JP | 4-233680 A | 8/1992 |
| JP | 5006449 A | 1/1993 |
| JP | 5-500917 | 2/1993 |
| JP | 5-314296 A | 11/1993 |
| JP | 6-163027 A | 6/1994 |
| JP | 06-171194 A | 6/1994 |
| JP | 6-333102 A | 12/1994 |
| JP | 7-098752 A | 4/1995 |
| JP | 7-271890 A | 10/1995 |
| JP | 8-106648 A | 4/1996 |
| JP | 8-118864 A | 5/1996 |
| JP | 8-179475 A | 7/1996 |
| JP | 8-220994 A | 8/1996 |
| JP | 8-262980 A | 10/1996 |
| JP | 9-016703 A | 1/1997 |
| JP | 9-034361 A | 2/1997 |
| JP | 9-091364 A | 4/1997 |
| JP | 9-192220 A | 7/1997 |
| JP | 9-223181 A | 8/1997 |
| JP | 9-274637 A | 10/1997 |
| JP | 10-105635 A | 4/1998 |
| JP | 10-268777 A | 10/1998 |
| JP | 11-135172 A | 5/1999 |
| JP | 11-162591 A | 6/1999 |
| JP | 11-180079 A | 7/1999 |
| JP | 11-276583 A | 10/1999 |
| JP | 11-316877 A | 11/1999 |
| JP | 2000-040119 A | 2/2000 |
| JP | 2000-272191 A | 10/2000 |
| JP | 2001-043301 A | 2/2001 |
| JP | 2001-075480 A | 3/2001 |
| JP | 2002-082120 A | 3/2002 |
| JP | 2002-517737 A | 6/2002 |
| JP | 2002518108 A | 6/2002 |
| JP | 2006-006696 A | 1/2006 |
| JP | 2007-507260 A | 3/2007 |
| JP | 4-233684 B2 | 3/2009 |
| WO | 91/04759 A1 | 4/1991 |
| WO | 92/17231 A1 | 10/1992 |
| WO | 1992017231 A1 | 10/1992 |
| WO | 93/12828 A1 | 7/1993 |
| WO | 94/08647 A1 | 4/1994 |

(56) References Cited

FOREIGN PATENT DOCUMENTS

| | | |
|---|---|---|
| WO | 94/12235 A1 | 6/1994 |
| WO | 94/15120 A1 | 7/1994 |
| WO | 95/24317 A1 | 9/1995 |
| WO | 95/28190 A1 | 10/1995 |
| WO | 98/02130 A1 | 1/1998 |
| WO | 99/60533 A1 | 11/1999 |
| WO | 9965548 A1 | 12/1999 |
| WO | 00/42678 A1 | 7/2000 |
| WO | 01/22348 A1 | 3/2001 |
| WO | 01/54055 A1 | 7/2001 |
| WO | 01/62322 A1 | 8/2001 |
| WO | 01/70304 A1 | 9/2001 |
| WO | 01/84542 A2 | 11/2001 |
| WO | 0195959 A1 | 12/2001 |
| WO | 02/11792 A1 | 2/2002 |
| WO | 02/13133 A1 | 2/2002 |
| WO | 02/092153 | 11/2002 |
| WO | 2002/092153 A2 | 11/2002 |
| WO | 2002/095675 A1 | 11/2002 |
| WO | 03/17915 A1 | 3/2003 |
| WO | 03/20598 A2 | 3/2003 |
| WO | 03/38738 A1 | 5/2003 |
| WO | 03/047659 A1 | 6/2003 |
| WO | 04/084795 A1 | 10/2004 |
| WO | 04/97715 A1 | 11/2004 |
| WO | 05/075010 A1 | 8/2005 |
| WO | 05/089835 A1 | 9/2005 |
| WO | 05/110387 A2 | 11/2005 |
| WO | 2005/110387 A2 | 11/2005 |
| WO | 06/113521 A2 | 10/2006 |
| WO | 2006/113521 A2 | 10/2006 |
| WO | 06/120182 A1 | 11/2006 |
| WO | 2006/120182 A1 | 11/2006 |
| WO | 07/039148 A1 | 4/2007 |
| WO | 07/107562 A2 | 9/2007 |
| WO | 2007/107562 A2 | 9/2007 |
| WO | 07/116090 A1 | 10/2007 |
| WO | 07/122253 A1 | 11/2007 |
| WO | 2008/150715 A1 | 12/2008 |
| WO | 09/15933 A1 | 2/2009 |

\* cited by examiner

MEDICAL DEVICE AND CARTRIDGE

CROSS-REFERENCE TO RELATED APPLICATIONS

This application is a divisional of U.S. application Ser. No. 13/148,868, filed Jan. 11, 2012 (pending), which is a 35 U.S.C. § 371 national stage application of International Patent Application PCT/EP2010/051804 (published as WO 2010/092156), filed Feb. 12, 2010, which claimed priority of European Patent Application EP 09152862.0, filed Feb. 13, 2009; this application further claims priority under 35 U.S.C. § 119 of U.S. Provisional Application 61/155,174, filed Feb. 25, 2009; the contents of which are incorporated herein.

The present invention relates to a medical device and cartridge.

Many medical devices are arranged to use detachable cartridges that carry consumable materials. These devices include systems such as pumps, injectors and nebulisers that deliver consumables such as anaesthetics, steroids or other drugs or fluids to a patient.

Clearly, where a range of possible consumable materials is available in similar cartridges (for example different concentrations of a drug) it is important that a cartridge including the appropriate consumable material for the situation is used. Typically this is achieved by selection of the appropriate cartridge by a qualified medical practitioner.

However, for patient-operated medical devices such as personal insulin injection systems, such qualified medical supervision is not regularly available and so use of the medical device and the selection of suitable consumable materials for it depends upon the patient themselves. Thus for example there is the potential for a patient to administer the wrong type, or wrong dose, of a drug into their body.

Prior art systems disclose mechanisms for marking such cartridges so that the medical device can evaluate the cartridge's content independently of the user. Such systems include barcodes on the cartridges (U.S. Pat. No. 6,859,673); binary patterns encoded by metallic or wirelessly inductive strips on the cartridge (U.S. Pat. No. 6,110,152, WO0213133, WO1992017231 or WO2007107562), or data represented by the value of one or more resistors (DE4020522, U.S. Pat. No. 6,743,202).

However, for very small, lightweight and cheap medical devices such as personal insulin injection systems, and similarly for small, lightweight and cheap containers such as insulin cartridges used by such personal insulin injections systems, the prior art discloses mechanisms that are either overly complex, require excessive space on the cartridge or are susceptible to damage or contamination (for example by a spillage of insulin, which is electrically conductive).

Therefore there is a requirement for an improved system comprising a machine-identifiable cartridge for use with a medical device.

In a first aspect, a cartridge is engageable with a medical device, the cartridge comprising an ordered arrangement of N electrical components each with different respective values of an electrical property, and an ordered arrangement of N conductors operably coupled to the ordered arrangement of the N electrical components.

Such an ordered arrangement may take the form of a topologically triangular or deltoid arrangement wherein each of the N components has a first electrical contact and a second electrical contact, the first electrical contact of each respective one of the N electrical components being connected to the second electrical contact of a respective other of the N electrical components to form N links, and each respective one of the N links is connected to a respective one of the N conductors.

In a specific form, the conductors and the ordered arrangement of N electrical components are mounted on a label that is affixed to an outer surface of the cartridge. The label may extend around the cartridge so that it overlaps itself. The conductors may be formed so as to extend around the cartridge circumferentially. In some embodiments, the ordered arrangement of N electrical components is positioned substantially at one end of the ordered arrangement of N conductors. By forming the label to overlap itself, a continuous or substantial continuous loop of conductors may be formed so as to cover the ordered arrangement of N electrical components. In embodiments where the number of N electrical components are larger than two, this ensures that the loop of conductors extend with no or only a slight gap in the circumferential direction, without the need for making a multilayer structure to provide the necessary connections to the N components.

In another aspect, a medical device arranged to receive a cartridge comprises for each of N conductors on the cartridge at least a first respective contact arranged to electrically couple with the corresponding conductor when the cartridge is engaged with the medical device; the medical device also comprises an evaluation means operable to evaluate the different respective values of an electrical property of N electrical components on the cartridge, wherein the N electrical components form an ordered arrangement which is operably coupled to the N conductors on the cartridge, and a switching arrangement operable to selectively electrically couple a respective pair of contacts to said evaluation means.

In a further aspect, a method of manufacturing a cartridge engageable with a medical device, comprising the steps of selecting a code, responsive to the intended contents of the cartridge, selecting a respective one of M possible values of an electrical property from each of N non-overlapping sets, associating with the cartridge an ordered arrangement of N electrical components operably coupled to an ordered arrangement of N conductors, wherein each component embodies a respective one of the selected values of the electrical property, and selecting a particular order of the N electrical components with respect to the ordered arrangement of N conductors, wherein the selected of values of electrical properties together with the selected order with respect to the N conductors of the N electrical components embodying these values signify in combination the selected code.

Further respective aspects and features of the invention are defined in the appended claims.

Embodiments of the present invention will now be described by way of example with reference to the accompanying drawings, in which.

A medical device and cartridge are disclosed. In the following description, a number of specific details are presented in order to provide a thorough understanding of the embodiments of the present invention. It will be apparent, however, to a person skilled in the art that these specific details need not be employed to practise the present invention. Conversely, specific details known to the person skilled in the art are omitted for the purposes of clarity where appropriate.

As a non-limiting example, a summary embodiment of the present invention comprises a pen-style personal insulin injector arranged to receive a pre-filled medicament cartridge, attached to which are three resistors, a first contact of each sharing a common connection and the second contact of each being connected to a respective conductive strip. The conductive strips are accessible by the injector when the cartridge is properly engaged with it. Each resistor is chosen to have a resistance value selected from a respective one of three non-overlapping sets of possible values, so that each resistor has a different value and that value is unique to its respective set. The selection of a value from a set is used to encode information relating to the contents of the cartridge. Likewise, the placement of each resistor within an ordered arrangement (for example, which resistor is connected to which conductive strip) is also chosen to convey information relating to the contents of the cartridge, as the use of distinct values from non-overlapping sets enables the relative positions of each resistor with respect to the conducting strips to be evaluated.

In this way a robust encoding of information about the contents of the cartridge can be conveyed in a compact manner. Complementary measures to mitigate against contamination include a non-conductive protective layer over the conductors that is punctured by contacts in the injector when the cartridge is engaged, an exposed conductor not connected to the components that indicates contamination if a subsequent electrical connection is found, and the use of components with complex impedance (resistance) such as capacitors, whose complex impedance is measured at an oscillating frequency where the electrical properties of the presumed contaminant (here, insulin) are less likely to affect measurement.

Figure 1:
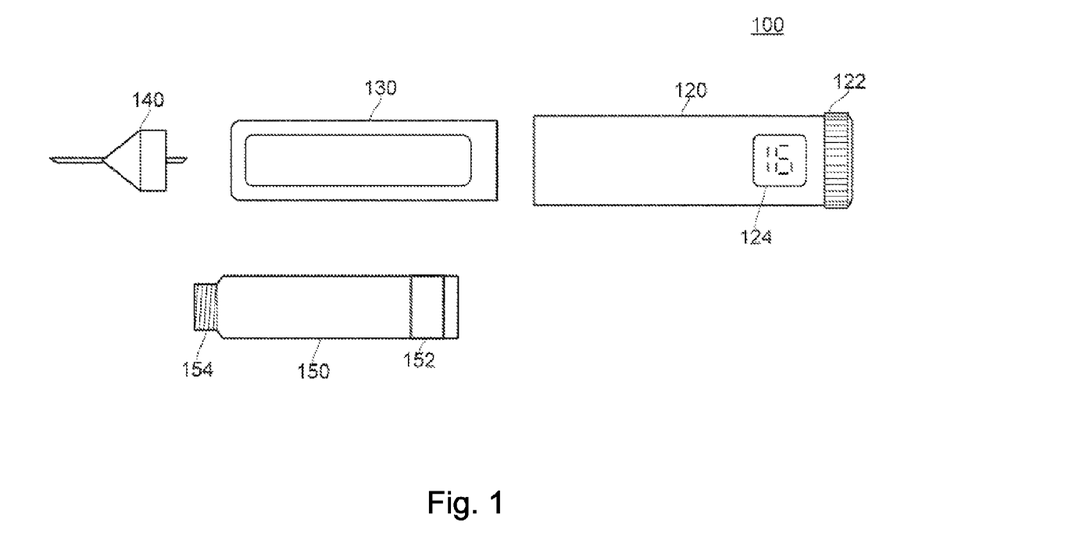
FIG. 1 is a schematic diagram of a medical device and a cartridge in accordance with an embodiment of the present invention.

Referring now to FIG. 1, in an embodiment of the present invention a medical device in the form of a personal insulin injector 100 comprises a main body 120 housing a dosing mechanism (not shown), a dose setting interface 122, and a user interface 124 for displaying information such as the currently set dosage.

The injector also comprises a detachable cartridge holder 130, into which a cartridge 150 may be inserted. The holder is then engaged with the injector housing, causing the cartridge to be engaged with the injector dosing mechanism of the injector. The cartridge 150 may be of the so-called 'plunger' type illustrated in FIG. 1, or may equally be a flexible or collapsible reservoir or any other suitable form.

A needle assembly 140 may then be attached to the cartridge and holder by the screw thread 154 of the cartridge, causing a rear-facing end of the needle to puncture a sealed aperture in the cartridge, thereby enabling a flow of insulin into the needle under the control of the dosing mechanism.

In addition, the cartridge comprises an encoding circuit 152 that embodies a code that can be evaluated by the injector.

Figure 2A:
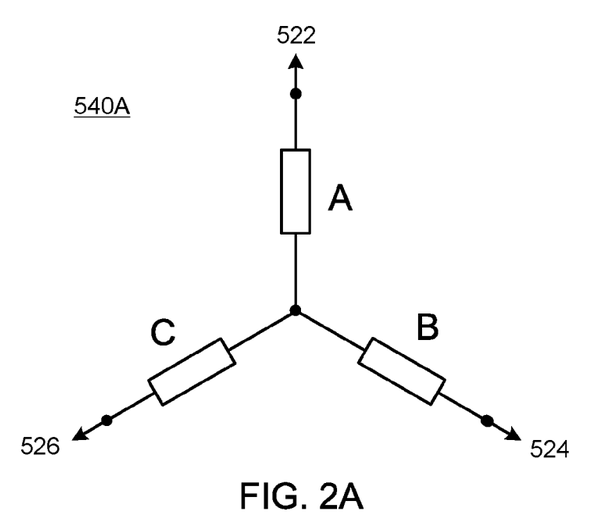
FIGS. 2A and 2B are schematic diagrams of ordered arrangements of components in accordance with embodiments of the present invention.
Figure 2B:
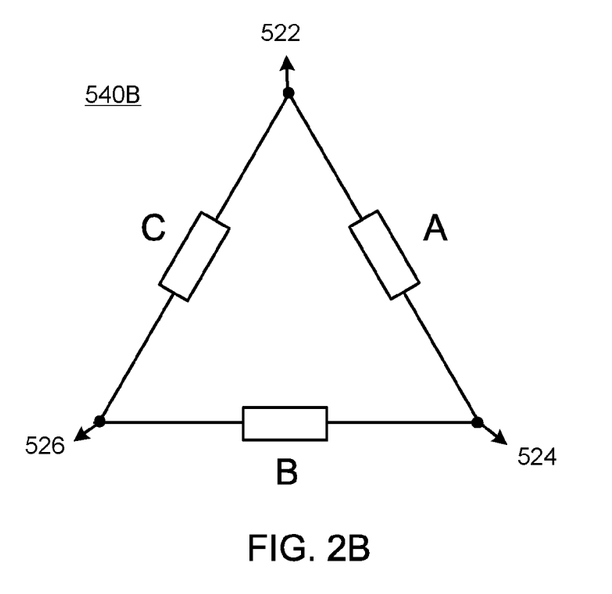

Referring now to FIGS. 2A and 2B, the encoding circuit comprises an ordered arrangement 540A, 540B of three electrical components (A, B and C), each having a particular and different value of an electrical property such as impedance (or complex impedance). Possible components include resistors, capacitors and/or inductances, or diodes (which have non-linear impedance).

FIG. 2A shows the three components arranged in a so-called 'star' configuration, in which one contact of each component shares a common connection.

FIG. 2B show the three components arranged in a polygonal (here triangular) configuration, in which a first contact of each component is connected to the second contact of one of the other components to form a closed chain.

In both configurations, three conductor strips (522, 524 and 526) are electrically coupled to the arrangement of components. In the star configuration, each conductor strip connects to the free contact of a respective component. In the triangular configuration, each conductor strip connects to a respective link between the first and second contacts of a pair of components. The conducting strips then typically form an ordered sequence of rings around some or all of the circumference of the cartridge 150.

Advantageously, this arrangement avoids the use of a common or ground conductor, thereby reducing the number of conductors required and hence both costs and the risk of such a common conductor becoming contaminated and compromising measurements of all the component values.

Data is encoded using the components in the following manner. Each of the three components (A, B and C) has a particular value of an electrical property that is selected from a respective one of three sets of possible values, and these sets do not overlap. As a non-limiting example, possible values of impedance may be as given as follows in Table 1:

TABLE 1

Three non-overlapping sets of three possible impedance values

| | Component | | |
|---|---|---|---|
| | A | B | C |
| Value 1 (Ohms) | 100 | 400 | 1600 |
| Value 2 (Ohms) | 200 | 800 | 3200 |
| Value 3 (Ohms) | 300 | 1200 | 4800 |

This gives $3^3=27$ possible unique combinations of values for the arrangements of A, B and C seen in FIG. 2A or 2B.

Notably, the possible values held by the components A, B or C are uniquely characteristic of those components (or the value sets with which the components are associated).

Consequently, therefore, the order in which the components are arranged with respect to the conductor strips (522, 524 and 526) can also be uniquely identified. For example, using successive conductor strips on a cartridge to test the impedances may result in values 100, 800, 1600 being evaluated (using example values from Table 1), meaning the components are arranged as A, B and C with respect to the conductors (for example as seen in FIGS. 2A and 2B). Meanwhile, testing of a different cartridge in the same way may result in values 800, 100, 1600, meaning the components are arranged as B, A and C with respect to the conductors.

Therefore the ordering of the components A, B and C with respect to the series of conducting strips can also be used to convey information. For three components, the respective order can be rotated three ways: (A, B, C), (C, A, B), (B, C, A), and these rotations can also be mirrored: (C, B, A), (B, A, C), (A, C, B).

The total number of possible unique combinations with respect to a fixed set of conductors for three components is therefore 27×6 or 162.

More generally, the set of six arrangements of A, B and C above are achieved by swapping successive pairs of components with respect to the three conductors, as follows:

This approach may then be generalised to more than N=3 components. For example, in the case of four components (A, B, C, D) in a star or square formation analogous to those in FIGS. 2A and 2B, with a corresponding four sets of non-overlapping values and four conductors, a total of 24 unique orderings with respect to the four conductors can be generated by successively swapping pairs of components in the above fashion. Notably, for four non-overlapping sets each of three values, there are $3^4=81$ possible unique combinations of values for any one arrangement of components A, B, C and D. Therefore the total number of possible unique combinations is 81×24=1,944.

It will be appreciated that optionally more than M=3 electrical property values may be available in each set, thereby further increasing the possible number of unique combinations.

Alternatively, fewer values may be used. Using fewer values simplifies evaluation, reduces requirements for component value tolerance and measurement accuracy, and/or improves robustness to contamination. For example, using four components with four non-overlapping sets each only having two possible electrical property values (e.g. as shown in the non-limiting example of Table 2 below), then there are $2^4=16×24=384$ unique combinations.

TABLE 2

| N = 4 non-overlapping sets of M = 2 possible impedance values | | | | |
|---|---|---|---|---|
| | Component | | | |
| | A | B | C | D |
| Value 1 (Ohms) | 100 | 400 | 1200 | 3200 |
| Value 2 (Ohms) | 200 | 800 | 1600 | 4800 |

In addition, it will be appreciated that unlike a system where each component may take any value from a single, larger set of possible values (for example where components A, B, C and D could each take any one of the eight values shown in Table 2, thereby giving 576 possible combinations), in embodiments of the present invention if one component value (or values for a pair of components) are affected by contamination, then identification of the other component values provides information about the contaminated component values by a process of elimination (e.g. if values 800, 1200 and 4800 are read accurately, then the final reading must either correspond to 100 or 200 for component A). This assists any attempt to resolve the value of the contaminated component, thereby making the code more robust to contamination.

Robustness may be further improved by the use of a redundant coding scheme. For example, in the case of the above arrangement of four components seen in Table 2, the values of components A and C may be correlated, as may those of B and D. In this way if any one component is compromised and returns a value outside the expected range of its set, the information is still available from the corresponding other component. The correlation of non-adjacent components (and by extension, non-adjacent conductors) reduces the risk of a contaminating spillage compromising both components or conductors of a correlated pair.

It will be appreciated that other coding schemes may also be apparent to the person skilled in the art.

Figure 3:
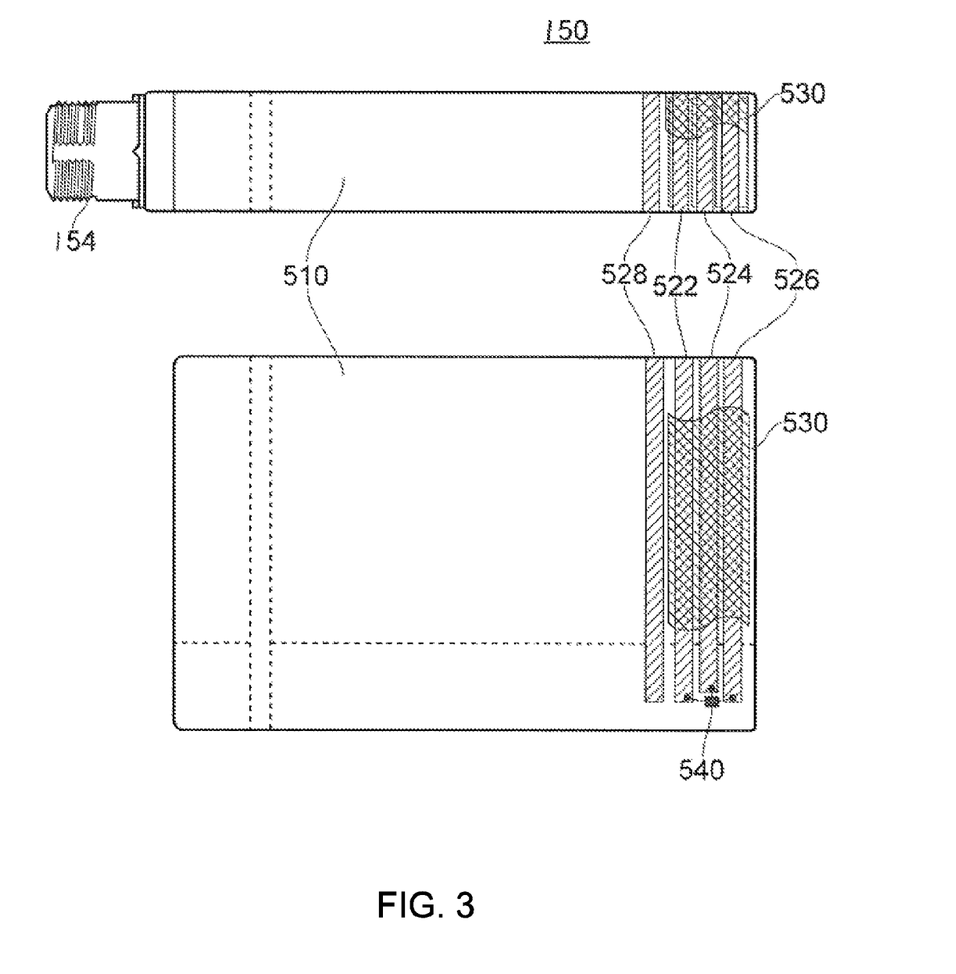
FIG. 3 is a schematic diagram of a labelled cartridge in accordance with an embodiment of the present invention.

Referring now to FIG. 3, in an embodiment of the present invention an ordered arrangement of components 540 (encompassing a star arrangement 540A or a polygonal arrangement such as a triangle or square 540B) is mounted on (e.g. affixed to) a label 510 using known techniques is and is appropriately connected to an ordered arrangement of conductors (522, 524, 526) that extend across the width of the label.

Optionally, the width of the label is such that it is greater than the circumference of the cartridge, so that when the label is wrapped around the cartridge an overlapping portion extends to cover the components and their connections to the conductor strips, thereby providing a degree of protection to the components from contamination or damage due to handling. This configuration has the additional benefit that the conducting strips then substantially encircle the cartridge, thereby removing the requirement for rotational alignment of the cartridge with electrical contacts in the medical device.

Alternatively, if the label does not overlap then the components may be covered by a non-conductive protective layer, and the conductors then also extended over this layer, thereby again substantially encircling the cartridge to the extent that the label encircles it. In this case connections to the conductors would be provided that extend out from under the protective layer to connect the components to the conductive strip.

Alternatively or in addition, the arrangement of components 540 may all be clustered, grouped or otherwise positioned at or near one end of the conductor strips, so that only a small proportion of the circumference of the cartridge corresponding to the components does not feature the conductors, as seen in FIG. 3.

It will be appreciated that consequently in an embodiment of the present invention the label 510 alone, comprising the encoding circuitry and conductors, may be provided separately to conventional cartridges, and only subsequently applied to such cartridges for example at a packaging plant at a later date.

Alternatively, the components and/or the conductors can be mounted (e.g. affixed) directly on the cartridge in a similar manner, again using known techniques. In this case again the components may be clustered at or near one end of the conductor strips, or may be covered by a protective layer over which the conductors extend.

In the case of mounting the circuitry and conductors on either the label or directly on the cartridge, in an embodiment of the present invention the components may be discrete components or may be part of an integrated circuit, or may be printed onto the label or cartridge (for example using resistive inks).

Likewise in the case of mounting the circuitry and conductors on either the label or directly on the cartridge, in an embodiment of the present invention a non-conductive protective layer or coating is then applied over the conductors, and optionally over the components. The coating serves to shield the conductors (and optionally components) from electrically conductive contamination such as a spillage of insulin forming a connection between two conductors and thereby affecting the measurement of the electrical properties of the components. In use, the corresponding measurement reading contacts in the medical device push or scrape through this layer to make electrical contact as the cartridge is engaged with the medical device, as explained later herein.

In an embodiment of the present invention, an additional so-called 'verification conductor' is provided that is not electrically coupled to the ordered arrangement of components, and is not covered by a protective layer. In the medical device an additional corresponding contact is also provided. The medical device can then determine whether there is any electrical connection between the additional contact and any of the measurement reading contacts in the medical device, thereby indicating whether a conductive contaminant may be on the surface of the cartridge or have impregnated the label, if present.

The medical device can then alert the user and/or prevent full engagement of the cartridge (for example by actuation of a blocking mechanism), enabling the user to remove the cartridge and attempt to clean off the contaminant.

Notably, in the case that the other conductors corresponding to the ordered arrangement of components are covered by a protective coating, such an electrical connection can be arranged to occur before the contacts of the medical device puncture the coating (as the contaminant will lie upon the coating), thereby allowing detection and removal of the contaminant before the protection of the coating is compromised.

In the medical device, measurement reading contacts are aligned to correspond with the conductors on the cartridge and make an electrical connection when the cartridge is engaged.

As noted previously, in the case that the conductors connected to the ordered arrangement of components are covered by a protective layer, the corresponding measurement reading contacts push through the protective layer to make electrical contact.

Figure 4A:
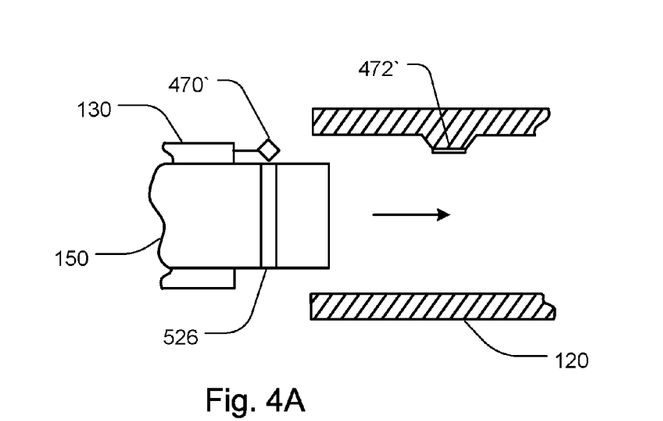
FIGS. 4A, 4B and 4C are schematic diagrams of electrical contact engagement means in accordance with embodiments of the present invention.

Referring now to FIG. 4A, where during engagement of the cartridge the motion of the cartridge holder retaining the cartridge is primarily axial with respect to the aperture that receives the cartridge, a bridging contact 470' mounted on the holder (similar, for example, to a relay contact) is arranged to encounter a protrusion 472' in the body of the medical device as the holder is pushed into place, so forcing the bridging contact 470' through the protective layer (not shown) to the conductor 526 below. The protrusion 472' comprises the measurement reading electrical contact, thereby making electrical contact with the conductor on the cartridge 150 via the bridging contact 470'. It will be appreciated that only one contact arrangement is shown in FIG. 4A for the purposes of clarity, and is not limiting.

Figure 4B:
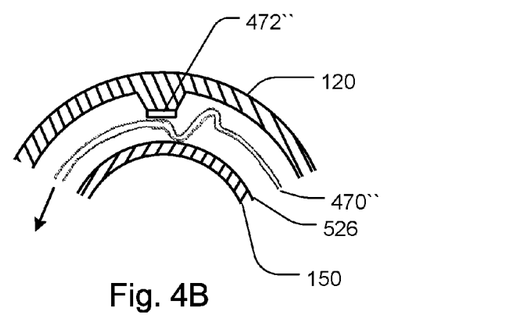

Referring now to FIG. 4B, where during engagement of the cartridge the motion of the cartridge holder retaining the cartridge is primarily rotational with respect to the aperture that receives the cartridge, a bridging contact 470" within the cartridge holder (such as, for example, a circle or arc of wire that has protrusions towards and away from the cartridge 150) is arranged to encounter a protrusion 472" in the body of the medical device as the holder is rotated, so forcing a portion of the bridging contact 470" through the protective layer (not shown) to the conductor 526 below. The protrusion 472" comprises the measurement reading electrical contact, thereby making electrical contact with the conductor of the cartridge 150 via the bridging contact 470". It will be appreciated that only one contact arrangement is shown in FIG. 4B for the purposes of clarity and is not limiting.

Alternatively, in a medical device that does not use a cartridge holder or where it is undesirable to use bridging contacts, other mechanisms to drive the measurement reading contacts thought the protective coating on the conductor strips of the cartridge will be apparent to the person skilled in the art.

Figure 4C:
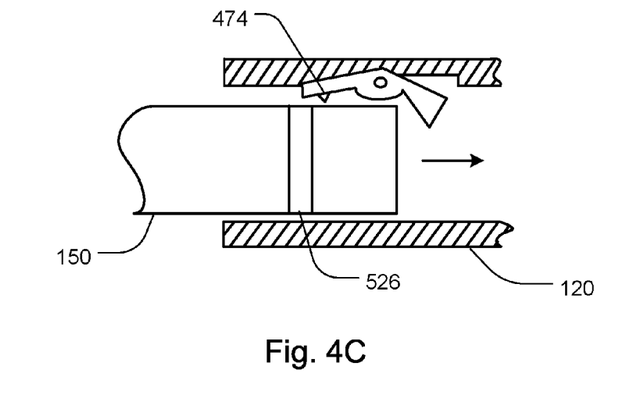

For example referring now to FIG. 4C, a measurement reading contact 474 is pivotally mounted within the medical device such that axial engagement of the cartridge with the medical device forces the measurement reading contact 474 through the protective layer (not shown) to the conductor 526 below. It will be appreciated again that only one contact arrangement is shown in FIG. 4C for the purposes of clarity and is not limiting.

In a conventional system that used a common ground connection, the electrical property of each component would be determined by switchably selecting between the components individually and measuring with respect to the ground connection. However to mitigate against contamination or damage to such a ground connection, in embodiments of the present invention there is no such common ground connection. As a result the values of the components must be evaluated by measuring components in combination.

Referring back to FIG. 2A, and using impedance as a non-limiting example, sequential measurements of impedance between conductors 522 and 524, 524 and 526, and finally 526 and 522 result in measurement of the series impedances of components A+B, B+C and C+A. Since impedances in series add together it is possible to calculate from these three measurements the individual impedances of components A, B and C.

Similarly, referring back to FIG. 2B, and again using impedance as a non-limiting example of electrical property, sequential measurements of impedance between conductors 522 and 524, 524 and 526, and finally 526 and 522 result in measurement of the impedance of component A in parallel with the series impedance of components B+C (i.e. A∥(B+C)), then B∥(C+A) and finally C∥(A+B). Again in principle these values can then be used to calculate the individual values of A, B and C.

Figure 5:
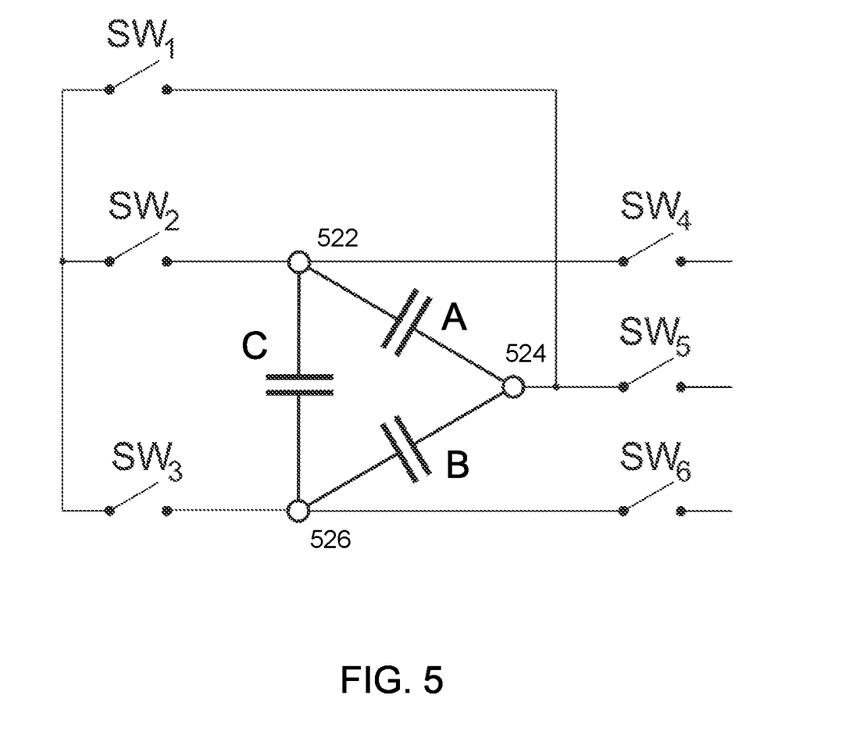
FIG. 5 is a schematic diagram of a switching arrangement in accordance with an embodiment of the present invention.

Referring now to FIG. 5, this second calculation can be simplified by a switching arrangement that short-circuits one of the impedances in the series. For example, by closing switches $SW_2$ and $SW_3$, component C is short circuited, and a measurement of A∥B can then be made by closing (i.e. measuring across) switches $SW_4$ and $SW_5$ (or alternatively by measuring across switches $SW_5$ and $SW_6$, which gives the commutative and hence equivalent measurement B∥A). Measurement of B∥C is achieved by closing switches $SW_1$ and $SW_2$ to short circuit component A and measuring across switches $SW_5$ and $SW_6$ or $SW_4$ and $SW_6$, whilst C∥A can be measured by closing switches $SW_1$ and $SW_3$ to short circuit component B and measuring across switches $SW_4$ and $SW_5$ or $SW_4$ and $SW_6$. From the measured values of A∥B, B∥C and C∥A, the individual values of A, B and C can be calculated.

This simplified calculation is less sensitive to component tolerances and measurement accuracy, and hence also to any residual contamination.

In addition, because each combined component value (A∥B, etc) can be measured using two possible switch combinations, contamination between adjacent conductors can be mitigated by using the alternatively available pair of switches (and hence alternative pair of conductors). Such contamination can be inferred, for example, if the difference between a measured value and each of the possible values in the corresponding value set falls outside a preset tolerance.

It will be appreciated that the above switching arrangement can be extended to four or more components, and so more generally measures values in a triangular, square or other polygonal arrangement of components by measuring across switches connected across a first component whilst short-circuiting all other components except a predetermined one in a series that is parallel to that first component.

Figure 6:
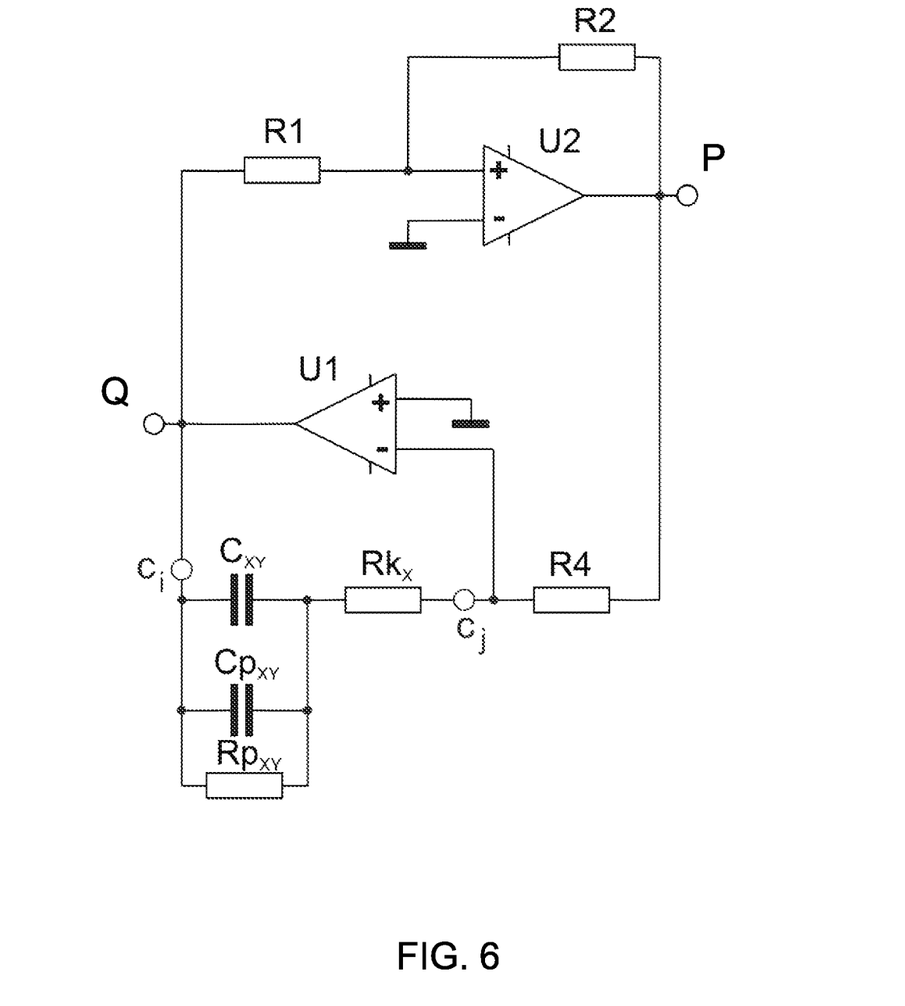
FIG. 6 is a schematic diagram of an oscillator circuit in accordance with an embodiment of the present invention.

Referring now to FIG. 6, in an embodiment of the present invention the components used have complex impedances (for example capacitors or inductors, rather than resistors). To measure the impedances (for example in the form of A∥B, as described above), each component is connected to an electronic integrator (U1)/comparator (U2) circuit, so forming an oscillator as seen in FIG. 6.

In FIG. 6 the generated frequency is determined primarily by resistor $R_4$ and the combined capacitor presented to the circuit by the switching arrangement $C_{XY}$ (such as, for example, A∥B). $R_{KX}$ is the comparatively small contact resistance, whilst $C_{PXY}$ and $R_{PXY}$ are the capacitive and resistive characteristics of any contaminants.

Notably, the dielectric properties of insulin (a likely contaminant) are not constant with frequency. Therefore by careful selection of the value of resistor R4 and optionally of the values in the N non-overlapping value sets used by the N components, a suitable range of resultant frequencies can be generated that occur where the dielectric properties of the insulin (or other cartridge payload if applicable) are substantially at their lowest, so further mitigating against the effects of contamination.

The frequencies so generated are measured at point P in FIG. 6, and may then be used to determine the presented combined component value (such as A∥B), and from a plurality of such measurements in sequence the individuals values of A, B C, etc can be obtained.

It will be appreciated that a similar measurement scheme may be used for the case where the electrical property of the components is itself a resonant or natural oscillating frequency. For example, the components may comprise crystals (such a quartz or another suitable piezoelectric crystal), each with a tuned frequency, or alternatively or in addition component pairs such as resistor/capacitor or inductor/capacitor giving rise to a natural oscillating frequency. In this latter case such frequency generating circuits may be treated as a single functional component for the purposes of the coding scheme described herein.

The information provided by the codes may vary in quantity and type. In the previous example herein of table 1, where three components and three associated non-overlapping sets each comprise three possible electrical property values, the total number of possible unique arrangements was 162. As a non-limiting example, a 1:1 redundancy in the coding may be applied (for example using component value correlation, as described previously), resulting in 81 usable codes.

64 of these codes may then be interpreted for example as a set of five binary flags, indicating the type of insulin and its concentration. Alternatively each code may be related to a look-up table held in a memory of the medical device, for example by using the code as part of a memory address, to give up to 81 different species of cartridge payload.

Finally, the medical device can act upon the information obtained using the code and inform the user of the species of payload within the cartridge. This may take the form of any suitable user interface, including alphanumeric text or an indicator light on the device, or wireless communication to a base unit, etc. Optionally the medical device may also evaluate whether the payload satisfies a usage condition; for example whether the payload has passed a sell-by date, or is the wrong concentration or type for the time of day or for a sequenced drug regime managed by the device. If the evaluation indicates that the payload is inapplicable, it may communicate a warning to the user via a suitable user interface, and/or may prevent administration of the payload to the user or require an explicit override from the user to do so.

Figure 7:
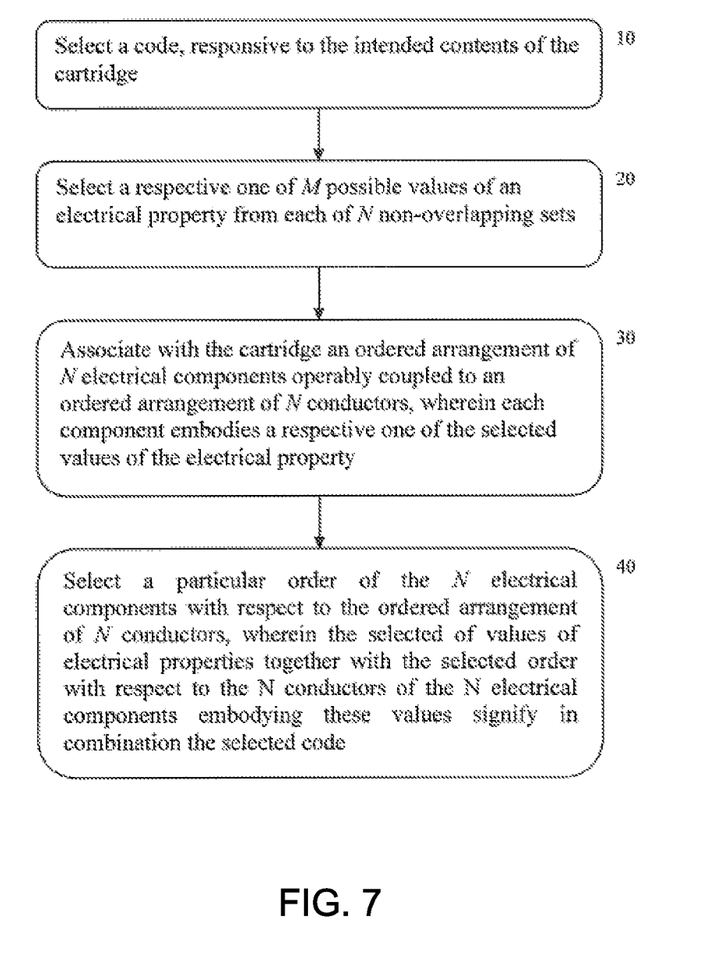
FIG. 7 is a flow diagram of a method of manufacture of a cartridge in accordance with an embodiment of the present invention.

Referring now to FIG. 7, a method of manufacturing a cartridge engageable with a medical device comprises:
  in a first step (10), selecting a code, responsive to the intended contents of the cartridge;
  in a second step (20), selecting a respective one of M possible values of an electrical property from each of N non-overlapping sets;
  in a third step (30), associating with the cartridge an ordered arrangement of N electrical components operably coupled to an ordered arrangement of N conductors, wherein each component embodies a respective one of the selected values of the electrical property; and
  in a fourth step (40), selecting a particular order of the N electrical components with respect to the ordered arrangement of N conductors, wherein
  the selected of values of electrical properties together with the selected order with respect to the N conductors of the N electrical components embodying these values signify in combination the selected code.

It will be apparent to a person skilled in the art that variations in the above method corresponding to manufacture of the various embodiments of the apparatus described above are considered within the scope of the present invention, including but not limited to:
  i. the components being arranged in a star or polygon topology;
  ii. the arrangement of components being positioned substantially at one end of the arrangement of conductors;
  iii. the electrical property being impedance;
  iv. the components used being one of resistors, capacitors, inductors, diodes or any component suitable to embody a specific value of the chosen electrical property;
  v. coating the conductors in an insulating, non-porous layer;
  vi. including a further conductor to detect contamination;
  vii. associating the components and conductors with the cartridge by use of glue or other fixing means, or alternatively
  viii. mounting the components and conductors on a label, and in this latter case
  ix. associating the components and conductors with the cartridge by affixing the label to the cartridge as a further step of manufacture, optionally so that the label overlaps itself to protect the (suitably positioned) components.

It will be appreciated that the apparatus disclosed herein may operate in part using conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a data carrier such as a floppy disk, optical disk, hard disk, PROM, RAM, flash memory or any combination of these or other storage media, or transmitted via data signals on a network such as an Ethernet, a wireless network, the Internet, or any combination of these of other networks, or realised in hardware as an ASIC (application specific integrated circuit) or an FPGA (field programmable gate array) or other configurable circuit suitable to use in adapting the conventional equivalent device.

The invention claimed is:

1. A method of preparing a series of uniquely coded cartridge variants engageable with a medical device, wherein, for any of said uniquely coded cartridge variants, performing the steps of:
   providing a cartridge;
   selecting a unique code, responsive to intended contents of the cartridge;
   selecting a value of an electrical property within a respective one of N non-overlapping sets of value ranges of the electrical property, wherein the N non-overlapping value ranges are common to the series of uniquely coded cartridge variants;
   designating a respective one of the N non-overlapping value ranges to each of N conductors;
   associating with the cartridge an ordered arrangement of N electrical components, each of the N electrical components having a first electrical contact and a second electrical contact, the arrangement of the N electrical components operably coupled to an arrangement of the N conductors so that the first electrical contact of each respective N electrical component connects to a respective one of the N conductors, and wherein each of N electrical component embodies a respectively corresponding one of the selected values of the electrical property; and
   selecting a particular order of the N electrical components with respect to the ordered arrangement of N conductors,
   wherein the selected values of electrical properties together with the selected order with respect to the N conductors of the N electrical components embodying these values signify in combination the selected unique code.

2. The method of preparing a series of uniquely coded cartridge variants engageable with a medical device according to claim 1, wherein within the ordered arrangement of N electrical components, the order of the N electrical components is arranged with respect to the ordered arrangement of N conductors to encode information.

3. The method of preparing a series of uniquely coded cartridge variants engageable with a medical device according to claim 1, wherein the electrical property is impedance.

4. The method of preparing a series of uniquely coded cartridge variants engageable with a medical device according to claim 1, wherein all of the N electrical components are one selected from the list consisting of:
   i. resistors;
   ii. capacitors;
   iii. inductors; and
   iv. diodes.

5. The method of preparing a series of uniquely coded cartridge variants engageable with a medical device according to claim 1, wherein the cartridge further comprises a conductor separate to the ordered arrangement of N conductors and not electrically coupled to the ordered arrangement of N electrical components on the cartridge.

6. The method of preparing a series of uniquely coded cartridge variants engageable with a medical device according to claim 1, wherein the conductors and the ordered arrangement of N electrical components are mounted on an outer surface of the cartridge.

7. The method of preparing a series of uniquely coded cartridge variants engageable with a medical device according to claim 1,
   wherein the conductors and the ordered arrangement of N electrical components are mounted on a label;
   the label is affixed to an outer surface of the cartridge; and
   the label extends around the cartridge and overlaps itself to cover the ordered arrangement of N electrical components.

8. The method of preparing a series of uniquely coded cartridge variants engageable with a medical device according to claim 1, further comprising a non-conductive protective layer applied over at least the N conductors.

9. The method of preparing a series of uniquely coded cartridge variants engageable with a medical device according to claim 1, wherein the series of uniquely coded cartridge variants exclusively comprises coded cartridge variants wherein the N electrical components have values of the electrical property selected from respective ones of said N non-overlapping value ranges of the electrical property.

* * * * *